United States Patent [19]

Skjak-Braek et al.

[11] Patent Number: 5,144,016

[45] Date of Patent: Sep. 1, 1992

[54] ALGINATE GELS

[75] Inventors: Gudmund Skjak-Braek; Storker Moe, both of Trondheim, Norway

[73] Assignee: Protan Biopolymer A/S, Drammen, Norway

[21] Appl. No.: 706,994

[22] Filed: May 29, 1991

[30] Foreign Application Priority Data

May 29, 1990 [NO] Norway .................................. 902386

[51] Int. Cl.⁵ .......................... C08B 37/07; B01J 13/00
[52] U.S. Cl. ....................................... 536/3; 252/315.3
[58] Field of Search ........................... 536/3; 252/315.3

[56] References Cited

U.S. PATENT DOCUMENTS 3,640,741 2/1972 Etes ............................................ 536/3

FOREIGN PATENT DOCUMENTS

57-036200 8/1980 Japan .

Primary Examiner—Nathan M. Nutter
Attorney, Agent, or Firm—Wenderoth, Lind & Ponack

[57] ABSTRACT

Superswelling cross-linked alginate gels which can swell strongly with a controllable swelling time in water, aqueous solutions of salts, proteins or the like. Process for the preparation of the alginate gels comprises the transferring of a water soluble alginate to an alginate gel, followed by a cross-linking reaction, reintroduction of non-gelling ions and drying the thus prepared gel.

10 Claims, 7 Drawing Sheets

ALGINATE GELS

The present invention concerns biocompatible, superswelling alginate gels, and a process for the preparation thereof.

Alginates are linear binary copolymers of D-mannuronic acid (M) and L-guluronic acid (G) of the formulas:

D-mannuronic acid

L-guluronic acid

The polymers are built up of blocks of M rich units, G rich units and mixed sequences of M- and G-units, so-called MG-blocks.

Alginates are isolated from marine brown algae and are used in the pharmaceutical, cosmetic, textile and food industry. The most common uses are based on the polyelectrolytic nature of the alginates, which forms the basis of their gelling properties and their ability to swell.

The commercially available sodium alginates are water soluble. When adding such alginates to a solution containing polyvalent ions, such as for example bivalent alkaline earth metal ions such as Ca, Sr and Ba or the trivalent Fe or Al ions, alginate gels having a defined form are produced. This is a result of a ionic cross linking of several alginate chains.

The alginate's ability to bind polyvalent cations selectively with raising affinity and thus its gelforming properties depend both on the monomer composition and the distribution of G units along the chain. Diaxially bound G units form binding sites for cations which are bound selectively in the following range: $Mg < Ni < Ca < Sr < Ba < Zn < Cd < Cu < Pb$ By addition of for example bivalent ions to a solution of alginate, a gel will be formed when the ions are bound to the sites between the G units and long sequences of such units are cross-linked with corresponding sequences in other polymer chains to form junction zones in the gel network. The alginate's G content will depend on the source from which the alginate is isolated. The common, commercially available alginates have a G content of approximately 40%. A high content of G-blocks gives an alginate of high affinity and selectivity for polyvalent cations. Such gels can be stored in water and weak salt solutions as well as in several organic solvents without a significant change of volume. After drying, the gels only take up water and swell to a small degree.

A gel can be defined as a cross-linked polymer, which has been swollen in water. In a ionic gel the degree of swelling will substantially be determined by the osmotic potential of the dissociable ions, which at equilibrium is in balance with the cross-linking forces in the gel network. By replacing the bivalent cross-linking ions in an alginate gel with dissociable monovalent ions, the number of cross-links in the gel will be reduced at the same time as the osmotic potential will rise and the gel will swell. By introducing covalent cross-links, all the cross-linking ions may be replaced by dissociable ions such as Na, K and $NH_4$ without the gel being dissolved.

For said sodium, potassium or ammonium gel the positive contribution to the swelling will substantially be a result of the dissociable ions. The swelling will be restricted by the number of covalent cross-links. Further, the degree of swelling can be manipulated by a controlled addition of gelforming ions such as Ca, Sr and Ba, as these ions will reduce the positive osmotic contribution and introduce ionic cross-links.

It is known, among other from [F. Ferrero, P. Campagna and N. Piccinini, Chem. Eng. Com., Vol. 15, p. 197-206 (1982)] to produce selective ion exchangers with a stable form, which has a reduced swellability and shrinkability, from Ca alginate beads by cross-linking the OH groups of which have been transferred to Na alcoholate groups, with epichlorohydrin.

From Japanese Patent 58-20999 is known a cross-linked alkali metal alginate as a component of a washing powder in replacement of phosphate. The cross-links are made with aldehydes such as formaldehyde or glyoxal or epoxy compounds such as epichlorohydrin.

It has now, according to the present invention, surprisingly been found that it is possible to prepare cross-linked alkali metal and ammonium alginate gels having superswelling properties. These gels which are characterized by a swellability of 10-300 times the volume in water and 2-70 times their volume in physiological salt solution with a controllable swelling time and retention of the original form after swelling.

The alginate gels according to the present invention which have an ability to swell of 50-200 times their volume in water are preferred. Especially preferred are the alginate gels according to the present invention which have an ability to swell 100 times their volume in water.

The alginates which may be used to prepare the gels according to the present invention, have a G block content in the area of 30-85% and the alginates and their G block content will be chosen in dependence of the proposed use.

The alginates according to the present invention have monovalent cations such as Na, K, Cs or $NH_4$, as ions bound to the carboxylic acid group and have covalent cross-links between the alginate chains, which cross-links are formed with cross-linking agents having at least two groups which can be reacted with OH groups.

Further, according to the present invention, there is provided a method for preparing said alginate gels which is characterized by the following steps:
  addition of an aqueous solution of an alginate to an aqueous salt solution comprising at least one polyvalent gelforming cation;
  replacement of the aqueous solvent with an organic solvent or mixture of solvents wherein the cross-linking agent is soluble;
  reaction of the alginate gel suspended in the organic solvent with a cross-linking agent;
  removal of the remaining cross-linking agent by washing with an organic solvent and/or water;
  replacement of gelforming cations with non-gel forming monovalent cations in the aqueous phase;

drying.

By transferring an aqueous solution of an alginate such as a Na, K, Cs or NH$_4$ alginate, especially a Na alginate to a salt solution comprising gelforming ions such as Ca, Sr, Ba, Al or Fe, a gel is formed with a defined form such as, for instance, beads, sheets, fibres or similar forms. It is especially preferred to use Ca$^{2+}$—ions for instance as a solution of CaCl$_2$.

It is suitable to work in a concentration range for the alginate solution of 0.8-5% w/v and to add this solution to a solution of the polyvalent gelforming cation, having a concentration in the range 10 mM-1M. In order to obtain a homogenous gel, it is suitable to add a non-gelforming salt such as NaCl or MgC$_2$ to the alginate solution in a concentration of from 1-4 times the equivalent amount of the cross-linking salt, which, for instance, can be CaCl$_2$.

Thereafter the water is substituted with an organic solvent or a mixture of solvents which can dissolve the cross-linking agent. The alginate chains in the gel thus formed are cross-linked by reaction with a cross-linking agent having reactive groups which can be reacted with OH-groups. Examples of such cross-linking agents are epichlorohydrin or other cross-linking agents as described in [Birnbaum et al., Biotechn. Letters, 3:393-400, (1982)]. It is especially preferred to use epichlorohydrin as cross-linking agent in a concentration from 0.1-4M. It is preferred to preform this reaction in the presence of CaCl$_2$, preferentially in a concentration range of 0.5-15 mM and to add NaOH in a concentration of 10-500 mM. In this instance a suitable solvent will be ethanol. The temperature for the cross-linking reaction is not critical, and thus it is preferred to conduct the reaction at room-temperature.

After the reaction is completed the organic solvent is replaced by water by elution. The polyvalent cations in the cross-linked alginate gel are replaced by monovalent cations. It is especially preferred to introduce Na ions by addition of Na$_2$EDTA in excess compared to the concentration of Ca ions in the gel. It appears to be suitable with concentrations of 50 mM in most cases.

The thus prepared cross-linked alginate gel is dried by adding a first portion of an organic solvent, especially one which can be mixed with water, such as acetone or lower alcohols such as methanol, ethanol or isopropylalcohol in an amount of 1-8, especially 3-8, times the gel volume in one or more portions.

This process is finished by a quick wash with a concentrated organic solvent and drying of the gel thus treated at room-temperature. It is especially preferred to conduct the final drying in a fluidized bed with gas, especially air of room-temperature under controlled conditions and/or with inert gas.

A preferred method according to this invention will be conducted by
- adding a 0.8-5% w/v aqueous solution of an alginate to an aqueous salt solution comprising at least one polyvalent gelforming cation in a concentration of 10 mM-1M, preferably in the presence of a non-gelling salt;
- replacing the aqueous solvent with an organic solvent or mixture of solvents wherein a cross-linking agent is soluble;
- reacting the alginate gel in the organic solvent with 0.1-4M concentration of a cross-linking agent, preferably in the presence of 0.5-15 mM CaCl$_2$ and 10-500 mM NaOH for 1-8 hours;
- removing the remaining cross-linking agent by washing with an organic solvent and/or water;
- replacing the gelforming cations with an excess of non-gelforming monovalent cations in aqueous solution;
- drying by replacing the aqueous solvent with an organic solvent, especially a solvent which is mixable with water, such as acetone, methanol, ethanol, isopropylalcohol, followed by drying of the alginate gel with air or an inert gas, preferably in a fluidized bed.

The alginate gel may be produced in a predetermined form, for example as beads, sheets, fibres, films or the like.

An especially preferred embodiment of the process according to the invention is:
- addition of an aqueous solution of a Na alginate, 1-3% w/v, to an aqueous solution of CaCl$_2$, 0.1-0.5M, with an addition of NaCl, 0.1-2M;
- replacement of the aqueous solvent with ethanol;
- reaction of the alginate gel suspended in the organic solvent, representing 3 volume parts with 0.5-2 volume parts of 100% epichlorohydrin, in the presence of 1 volume part 0.1M CaCl$_2$ and 1 volume part 10-500 mM NaOH at room-temperature for 1-8 hours;
- removal of the remaining cross-linking agent by washing with ethanol;
- replacement of the Ca ions with Na ions by addition to 51 20-500 mM sodium EDTA in an aqueous phase;
- drying by addition of ethanol in a total amount of 6 times the volume of the gel in several portions with equilibration in between and drying at room-temperature with air.

The beads may be produced by letting a sodium alginate solution fall dropwise into a solution of a polyvalent gel-forming cation. The size of the beads can be regulated by using a coaxical air stream to blow off the beads. The diameter of the beads may thus be adjusted to the proposed use, but will usually lie in the area of from 100-4000 $\mu$m (0.1-4 mm) in wet condition. In dry condition the diameter of the beads will correspondingly be in the range from 20 $\mu$m-100 $\mu$m.

The swellability of the gel depends especially on the degree of cross-linking. This will depend on several factors, among other, the reaction time for the cross-linking reaction, the proportions of the amount of cross-linking agent and alginate gel, and pH.

Other features of the invention will appear from the appended claims.

In the following the invention shall be elucidated through preparative examples and examples showing the special properties of the gel according to the invention.

EXAMPLE 1

Preparation of Sodium Alginate Gel Beads with a Swellability of 100 v/v$_o$.

A solution of sodium alginate 2% w/v in a 0.2M NaCl solution was pressed through a cannula and the drops fell into a solution of 0.1M CaCl$_2$ and 0.2M NaCl. The diameter of the beads were adjusted to be 1.7 mm by using a coaxial air stream.

After collecting the beads were filtered from the water and added to 96% (v/v) ethanol. The system was left for 30 min. in order to obtain a constant ethanol concentration in the beads. This was repeated 5 times to obtain a sufficiently high ethanol concentration in the beads. The volume of the beads was measured and determined to be 3 volume parts.

One volume part of 0.1M CaCl$_2$ in aqua dest. was added as well as one volume part of NaOH in aqua dest. After equilibration two volume parts of 100% epichlorohydrin were added and pH was measured until the value of 12.51 was registered by the pH meter. The reaction was continued in a pH stat titration system with a set point 0.1 pH units below the originally measured value.

[pH stat system: Radiometer PHM 63 pH.meter connected to a Radiometer TTT 60 titrator and a Radiometer G202C pH measuring electrode and K401 reference electrode]. The titrand was 0.1M NaOH in destillated water.

After 4 hours and 50 minutes, 0.71 ml NaOH had been added per ml of the original bead/ethanol suspension and the reaction was terminated by addition of 1M HCl in distilled water until pH 7 was reached.

The beads were transferred to a washing column and washed with 2 liters of 96% ethanol in order to remove non-reacted epichlorohydrin. Thereafter the beads were washed with water and added to 5 liters of 50 mM Na$_2$EDTA at pH 7 overnight to remove calcium. The beads were then washed with water to remove EDTA.

To 100 ml of a suspension of the beads in water were added 70 ml aqua dest. and thereafter 96% ethanol in four portions of 180, 180, 150 and 100 ml with 0.5-1 hour equilibration between each addition. The ethanol was added slowly while stirring. The fluid was filtered from the beads and these were washed with 96% ethanol for 1 minute and filtered with suction. The beads were dried with room temperature air in a fluidized bed.

Figure 1A:
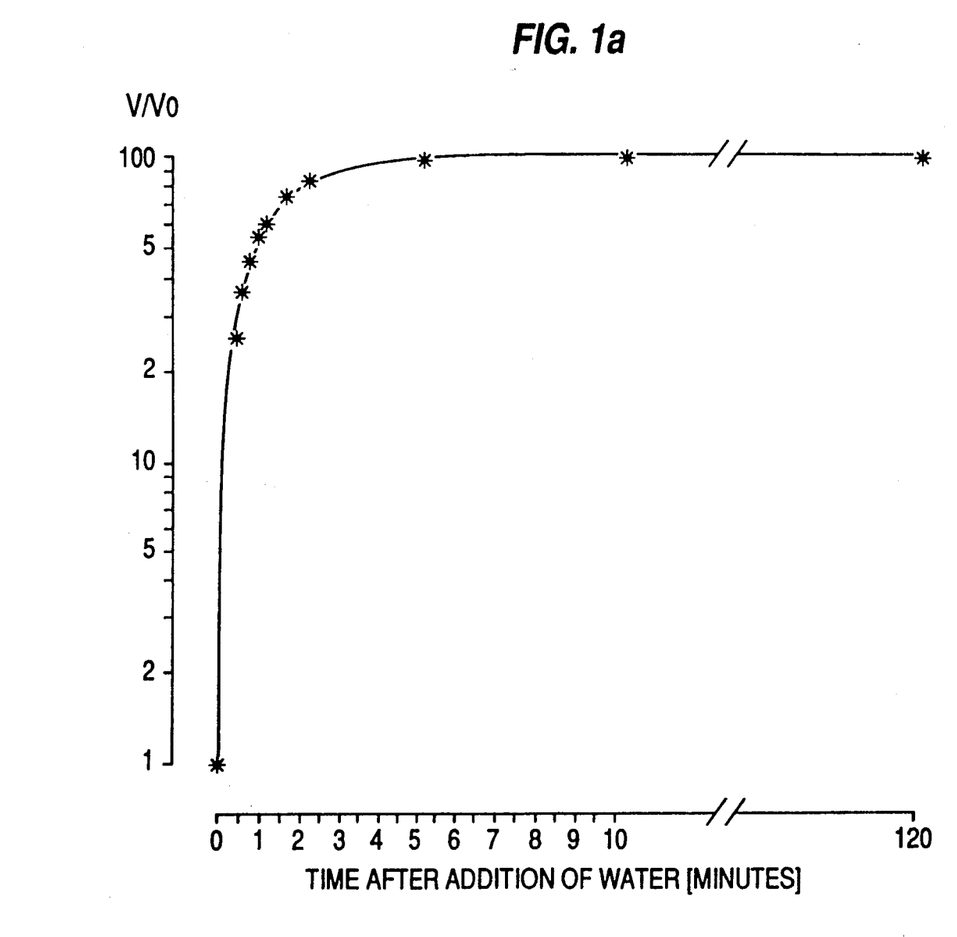
FIG. 1a shows the swellability in water of the gel beads prepared in Example 1.

The thus prepared beads had a swellability in water of 100 v/v$_o$ as appears from FIG. 1A.

Figure 1B:
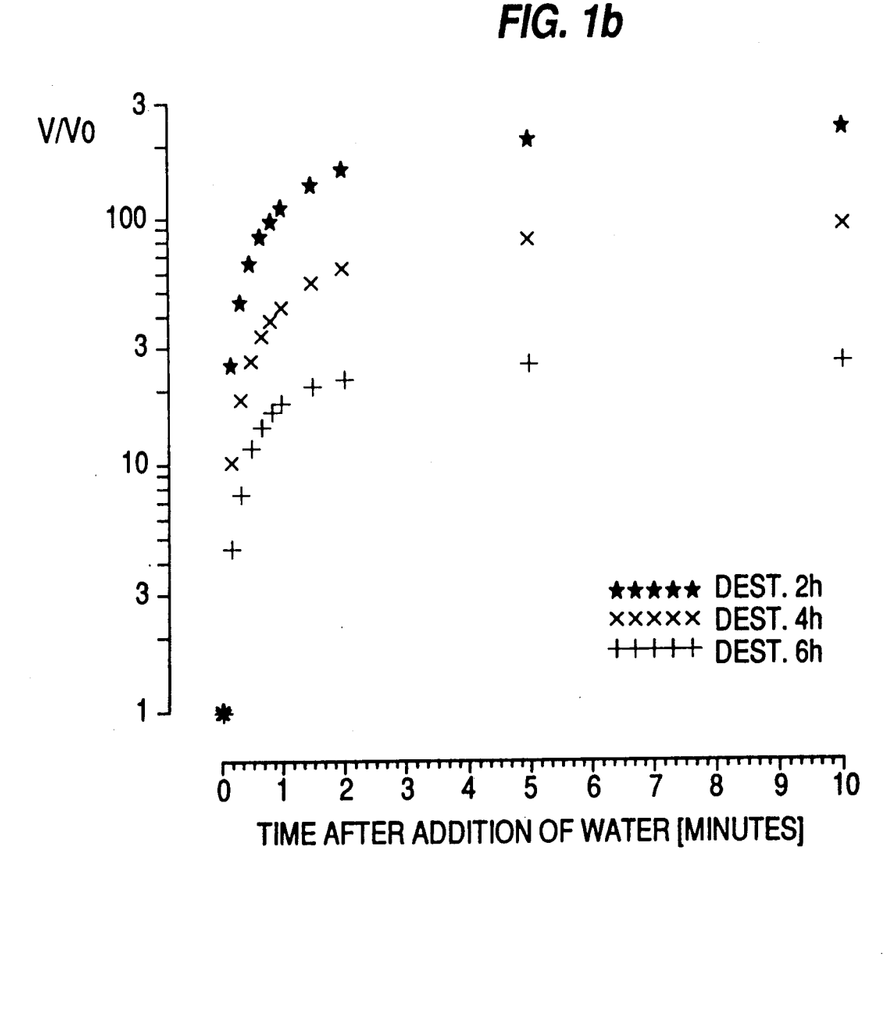
FIG. 1b shows ht swellability in water of the gel beads prepared in Example 1 dependent upon the reaction time.

FIG. 1B shows the swellability in water in dependence of the reaction time for beads prepared as described in Example 1, but with a reaction time of 2, 4 or 6 hours for the cross linking reaction.

Figure 1C:
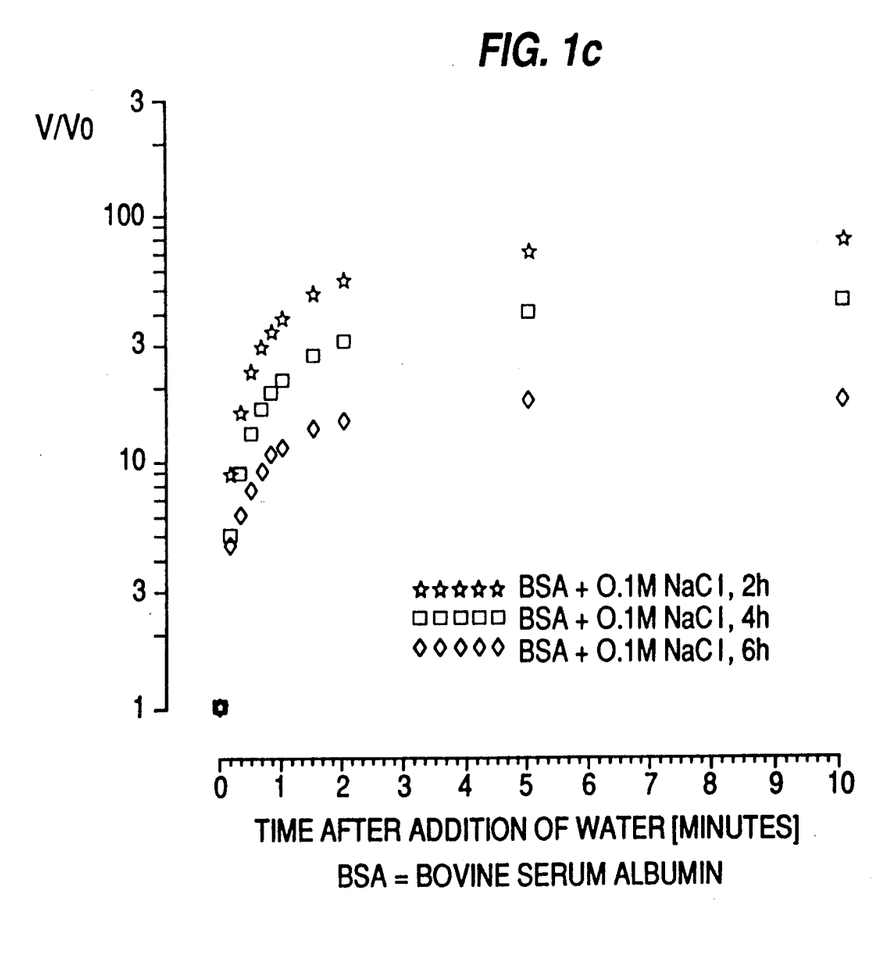
FIG. 1c shows the ability of the gel beads of Example 1 to swell in protein solutions dependent on the time of the cross-linking reaction.

FIG. 1C shows the ability to swell in protein solutions, in the present case in a solution of Bovine Serum Albumin (BSA), in dependence of the time of the cross-linking reaction for beads prepared as described for FIG. 1B above.

EXAMPLE 2

Preparation of Beads Having Different Swellabilities in Dependence of the Epichlorohydrin Concentration Used.

Figure 2:
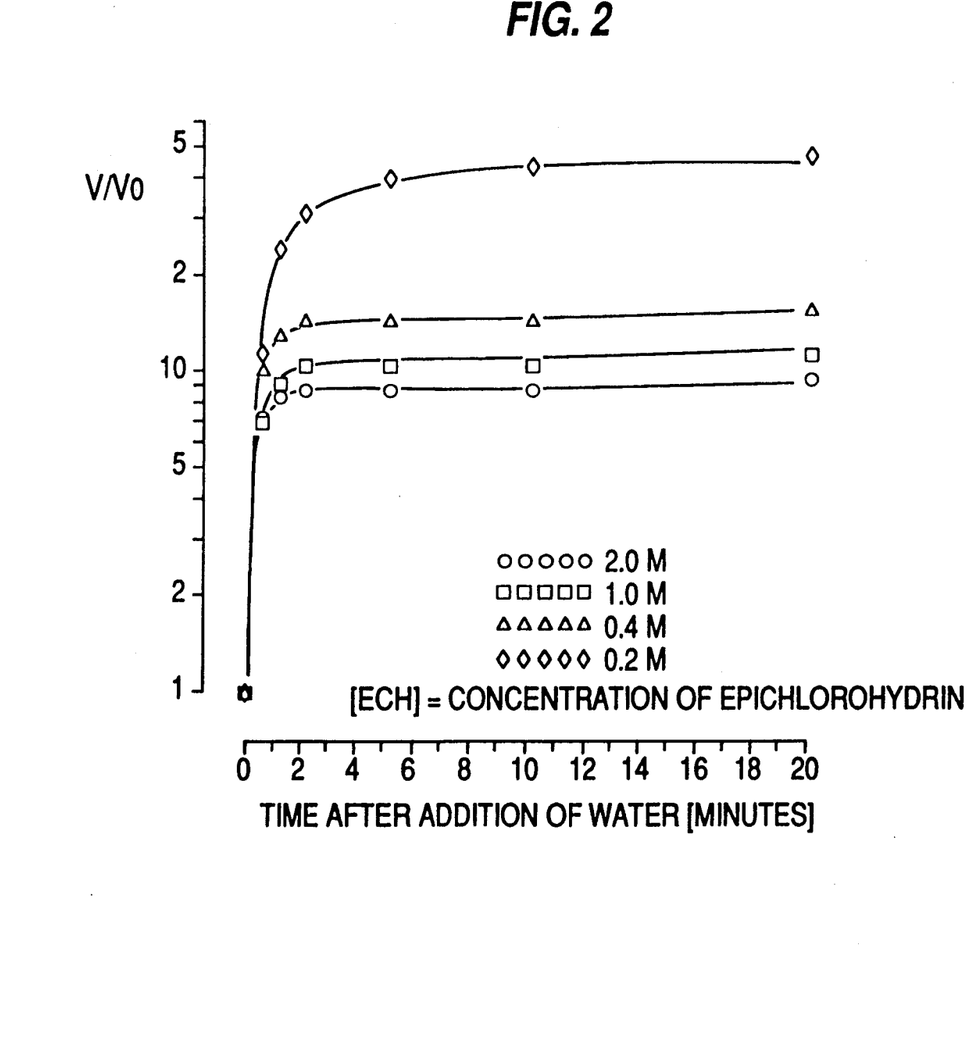
FIG. 2 shows the swellability of the gel beads of Example 2 dependent on the epichlorohydrin concentration.

As described in example 1, sodium alginate gel beads having a diameter of 2 mm were prepared from an alginate (having a content of 68% guluronic acid). The cross-linking reaction was performed with 0.05M NaOH at 20° C. and with different epichlorohydrin concentrations within the range of 0.2-2M. The achieved swellability in dependence of the epichlorohydrin concentration will appear from FIG. 2.

Figure 3:
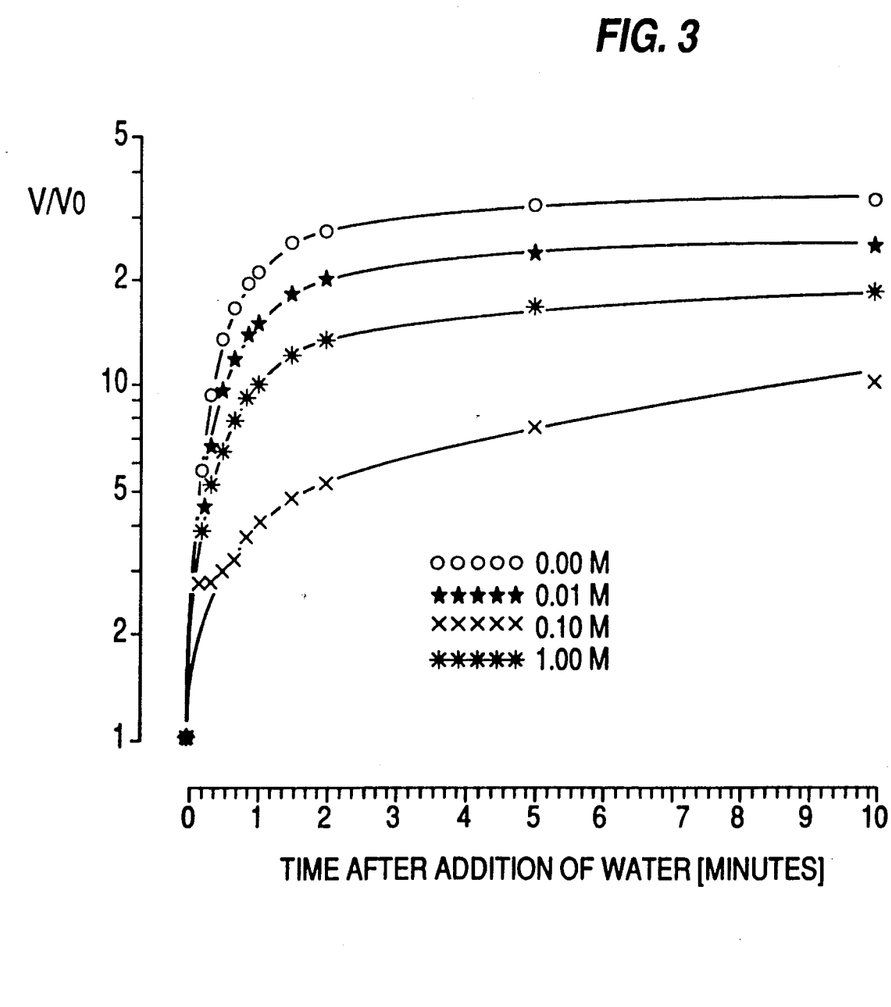
FIG. 3 shows the swelling of sodium alginate beads in saline solution dependent on salt concentration.

FIG. 3 shows the swelling of sodium alginate beads in saline solution in dependence of the salt concentration.

Figure 4:
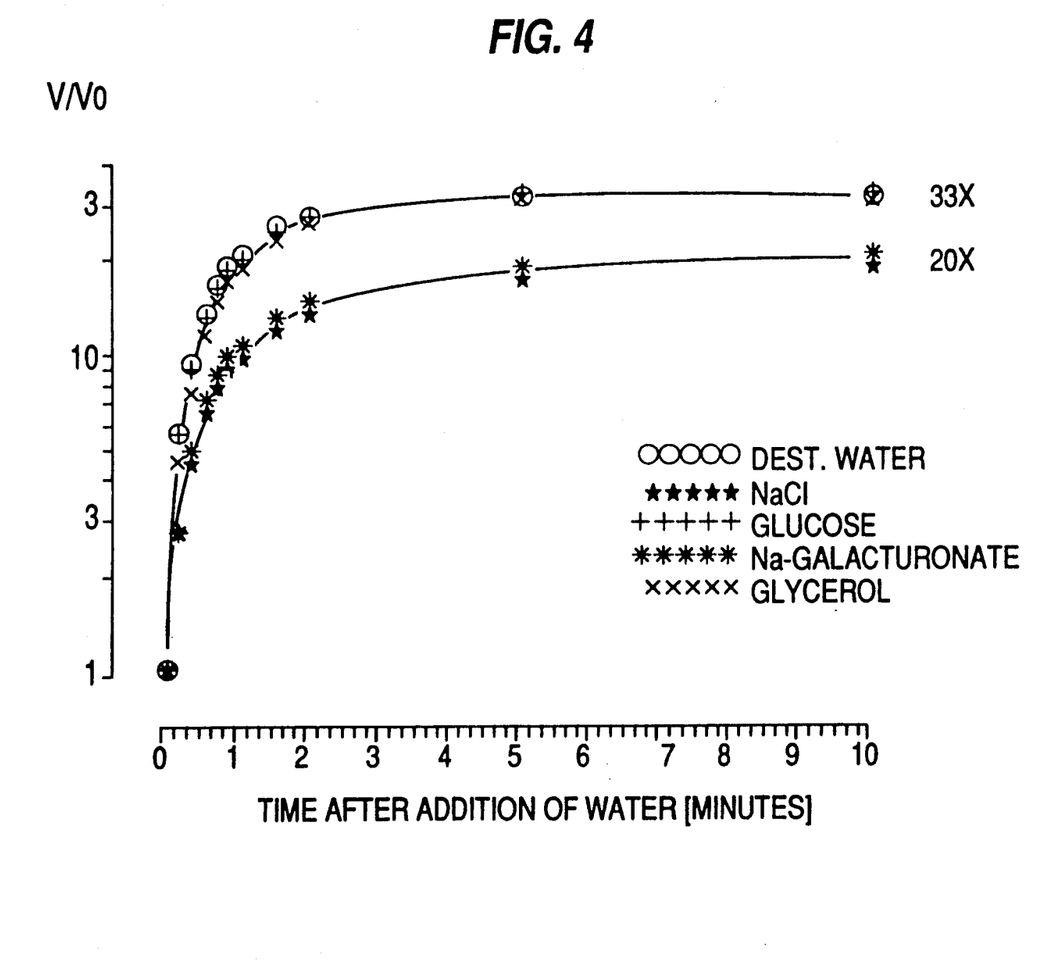
FIG. 4 shows the swelling of the beads in aqueous solutions of glucose, sodium galacturonate and glycerol.

FIG. 4 shows the swelling of the beads in aqueous solutions of glucose, sodium galacturonate and glycerol.

Figure 5:
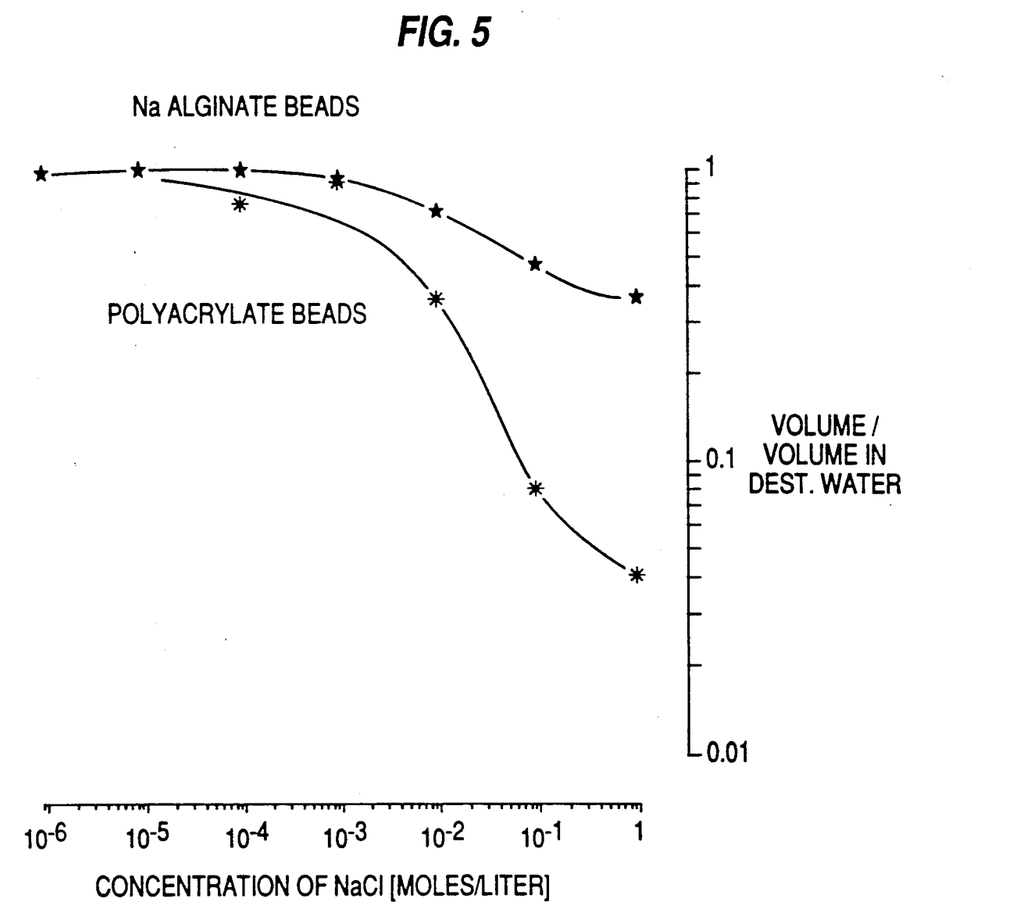
FIG. 5 shows the swellability of the sodium alginate beads of the invention int he saline solution compared with the swellability of polyacrylic beads dependent on salt concentration.

FIG. 5 shows the swellability of the sodium alginate beads according to the present invention in saline solution compared with the swellability of polyacrylic beads in dependence of the salt concentration. As appears from this figure, the sodium alginate beads still have a good swellability at higher salt concentrations, whereas the swellability of the polyacrylic acid beads declines substantially.

EXAMPLE 3

Preparation of a Macrogel.

Calcium alginate gels were prepared by mixing sodium alginate (1.5%) and CaEDTA (15 mM) in the presence of (80) mM glucono-δ-lactone. The dimension in thickness was 3 mm. The gel was transferred to an ethanol form and cross-linked with 0.5M epichlorohydrin at 20° C. for 6 hours as described for the beads. Calcium was replaced by sodium through dialysis against Na$_3$EDTA and the gel was dried to a film with a thickness of about 0.5 mm.

One special advantage with the alginate gels according to this invention is that they swell strongly, but controllably during a very short period of time in water, waterbased solutions or polycomponent systems, where one of the components is water. In one minute 80% of the solution will be absorbed.

Another advantage with the alginate gels according to the invention is that they are biocompatible and non-toxic.

A further advantage with the alginate gels according to the present invention is that they have a very high capacity of binding water. They can absorb 10-300 times their volume of water. For most uses it will be suitable to employ alginate gels according to the present invention which can absorb from 50-200 times their volume in water. Especially preferred are the alginate gels which swell 100 times their volume in water.

A further advantage with the alginate gels according to this invention is that they can swell in saline solutions, for example in physiological saline solution, with a swelling capacity of from 2-70 times. The swellability in saline solution will depend on the concentration of the salt solution.

Another advantage with the alginate gels according to the present invention is that they remain easy to handle after having absorbed the fluid, as they keep their original solid form even though their size is increased.

A further advantage is that the alginate gels according to the present invention can be regenerated after use.

A further advantage with the alginate gels according to the present invention is that they can be used for uptake of an active ingredient.

The alginate gels according to this invention can be used in all areas where a rapid uptake of a waterbased fluid is desirable, such as in diapers, tampons, woundhealing materials or the like. The alginate gels are also usable in areas where a rapid swelling in dependence of moisture is desirable. An example of this is a moisture sensitive packing material. Other uses are as absorbing means to remove water from polycomponent systems such as oil/gas/water mixtures as are encountered when drilling for oil and gas in the North Sea. Also in agriculture to remove water in manure. Another possible use is as a drying agent for gas or as a drying agent when keeping and/or storing medicaments.

Another especially suitable use of the alginate gels according to the invention is for the uptake of active substances such as medicaments, biocides, proteins or the like in order to prepare an administration form with a slow, diffusion controlled release. In this case the alginate gel, for instance in the form of beads, will be swelled in a solution of the active ingredient and thus absorb the solution. The water is removed through a following period of drying. The active ingredient remains inside the alginate gel structure. Prior to release the gel is again swelled in water and this will lead to a diffusion controlled release of the active ingredient.

It is further possible to contemplate a use of the alginate gels formed as microparticles for combatting vermin, where the particles may be carrying a means attractive for a special species, for example a bark beetle. After the animal has eaten the gel this will swell and result in the death of the animal.

Another possible use of the gels is as an appetite inhibitor for weight reduction, based on its swelling properties.

We claim:

1. A covalently cross-linked alkali metal and ammonium alginate gel having a swellability of 10-300 times its volume in water or 2-70 time its volume in physiological saline solution while retaining its original shape.

2. An alginate gel according to claim 1 characterized in having an ability to swell 50-200 time s it original volume in water.

3. An alginate gel according to claim 2 characterized in having an ability to swell 200 times its original volume in water.

4. A process for the preparation of a cross-linked alkali metal or ammonium alginate gel which comprises
   (a) adding an aqueous solution of an alginate to an aqueous saline solution comprising polyvalent gelforming cations;
   (b) replacing the aqueous solvent with an organic solvent or mixture of organic solvents wherein a cross-linking agent is present;
   (c) reacting the alginate gel suspended in said organic solvent or solvent mixture with a cross-linking agent;
   (d) removing the remaining cross-linking agent by washing with an organic solvent, water or with both an organic solvent and water in several steps;
   (e) replacing gelforming cations with non-gelforming monovalent cations in aqueous phase; and
   (f) drying the thus obtained product.

5. A process according to claim 4 wherein the alginate gel is dried by replacing the aqueous phase with an organic solvent or mixture of organic solvents, followed by drying in air or with an inert gas.

6. A process according to claim 5 wherein said organic solvent or organic solvent mixture is miscible with water.

7. A process according to claim 4 which comprises
   (a) adding a 0.8-5% w/v aqueous solution of an alginate to an aqueous salt solution comprising polyvalent gelforming cations in a concentration of 10 mM-1M, in the presence of a non gelling salt;
   (b) replacing the aqueous solvent with an organic solvent or mixture of organic solvents in which a cross-linking agent is soluble;
   (c) reacting the alginate gel in said organic solvent or organic solvent mixture with 0.1-4M concentration of a cross-linking agent for 1-8 hours;
   (d) removing the remaining cross-linking agent by washing with an organic solvent, water or with both an organic solvent and water in several steps;
   (e) replacing the gelforming cations with an excess of non-gelforming monovalent cations in aqueous solution; and
   (f) drying the resultant product by replacing the aqueous solvent with an organic solvent which is miscible with water followed by drying of the alginate gel with air or an inert gas in a fluidized bed.

8. A process according to claim 7 wherein in step (c) the reaction is in the presence of 0.5-15 mM $CaCl_2$ and 10-500 mM NaOH.

9. A process according to claim 7 wherein the organic solvent in step (f) is selected from the group consisting of acetone, methanol, ethanol and isopropylalcohol.

10. A process according to claim 4 which comprises
    (a) adding an aqueous solution f a sodium alginate, 1-3% w/v, to an aqueous solution of $CaCl_2$, 0.1-0.5M, with addition of NaCl, 0.1-2M;
    (b) replacing the aqueous solvent with ethanol;
    (c) reacting the alginate gel suspended in the organic solvent, representing three volume parts, with 0.5-2 volume parts epichlorohydrin, int he presence of 1 volume part of 0.1M $CaCl_2$ and 1 volume part 10-500 mM NaOH at room temperature for 1-8 hours;
    (d) removing the remaining cross-linking agent by washing with ethanol;
    (e) replacing the Ca ions with Na ions by adding to 20-500 mM $Na_2EDTA$ in aqueous phase; and
    (f) drying the resultant gel by adding ethanol in a total amount of 6 times the gel volume in several portions with equilibration between the addition of each portion and drying the gel at room temperature.

* * * * *